United States Patent
Kornberg et al.

(10) Patent No.: US 11,529,443 B2
(45) Date of Patent: Dec. 20, 2022

(54) APPARATUS AND METHOD FOR CEREBRAL MICRODIALYSIS TO TREAT NEUROLOGICAL DISEASE, INCLUDING ALZHEIMER'S, PARKINSON'S OR MULTIPLE SCLEROSIS

(71) Applicant: Cognos Therapeutics Inc., Los Angeles, CA (US)

(72) Inventors: Roger Kornberg, Atherton, CA (US); Yehoshua Shachar, Santa Monica, CA (US); Thomas Chen, La Canada Flintridge, CA (US)

(73) Assignee: Cognos Therapeutics Inc., Inglewood, CA (US)

(*) Notice: Subject to any disclaimer, the term of this patent is extended or adjusted under 35 U.S.C. 154(b) by 729 days.

(21) Appl. No.: 16/064,927

(22) PCT Filed: Dec. 27, 2016

(86) PCT No.: PCT/US2016/068725
§ 371 (c)(1),
(2) Date: Jun. 21, 2018

(87) PCT Pub. No.: WO2017/117138
PCT Pub. Date: Jul. 6, 2017

(65) Prior Publication Data
US 2019/0009014 A1    Jan. 10, 2019

Related U.S. Application Data

(60) Provisional application No. 62/271,866, filed on Dec. 28, 2015.

(51) Int. Cl.
*A61M 27/00*    (2006.01)
*A61M 1/16*    (2006.01)
(Continued)

(52) U.S. Cl.
CPC ............ *A61M 1/16* (2013.01); *A61M 1/14* (2013.01); *C07K 16/18* (2013.01);
(Continued)

(58) Field of Classification Search
CPC ........ A61M 1/14; A61M 1/16; A61M 1/3618; A61M 27/006; A61M 2201/0464; A61M 2210/0693
See application file for complete search history.

(56) References Cited

U.S. PATENT DOCUMENTS

6,056,725 A * 5/2000 Elsberry ............ A61M 25/0068
604/151
2003/0225067 A1* 12/2003 Stendel .............. A61B 5/14525
514/222.5
(Continued)

*Primary Examiner* — Benjamin J Klein
(74) *Attorney, Agent, or Firm* — Marcus C. Dawes; Daniel L. Dawes (57) ABSTRACT

An apparatus for performing cerebral micro-dialysis to treat neurological disease of a patient's brain includes a catheter for implantation in or near the patient's brain, an implantable pump communicated with the catheter to transport cerebrospinal fluid (CSF) from the patient, which CSF contains diseased cells or biomolecules associated with the neurological disease, and an implantable separation device communicated with the pump wherein the diseased cells or biomolecules are removed, where the separation apparatus includes a dialysis membrane impregnated with an antibody, a reversible electrostatic filter, and/or a magnetic field effect fractionation chamber wherein a magnetically-tagged antibody scavenges and aids in the removal of circulating diseased cells or biomolecules from the CSF.

31 Claims, 7 Drawing Sheets (51) Int. Cl.
 *A61M 1/14* (2006.01)
 *C07K 16/18* (2006.01)
 *G01N 33/68* (2006.01)

(52) U.S. Cl.
 CPC ....... *G01N 33/6896* (2013.01); *A61M 27/006* (2013.01); *A61M 2202/0464* (2013.01); *A61M 2210/0693* (2013.01); *C07K 2317/24* (2013.01); *G01N 2333/4709* (2013.01); *G01N 2800/2821* (2013.01); *G01N 2800/2835* (2013.01); *G01N 2800/52* (2013.01)

(56) References Cited

U.S. PATENT DOCUMENTS

| | | | |
|---|---|---|---|
| 2004/0030279 A1* | 2/2004 | Rubenstein | A61M 60/882 604/9 |
| 2006/0030056 A1* | 2/2006 | Fort | G01N 33/54333 436/524 |
| 2008/0181821 A1 | 7/2008 | Jung | |
| 2009/0047297 A1* | 2/2009 | Kim | B03C 1/288 424/184.1 |
| 2009/0131850 A1* | 5/2009 | Geiger | A61M 27/006 604/9 |
| 2009/0277850 A1* | 11/2009 | Adams | A61M 1/1678 210/798 |
| 2010/0305492 A1* | 12/2010 | Lad | A61M 25/0026 604/9 |
| 2011/0098623 A1* | 4/2011 | Zhang | B03C 1/01 604/5.02 |
| 2012/0095325 A1* | 4/2012 | Wei | A61B 5/0042 600/411 |
| 2012/0238936 A1* | 9/2012 | Hyde | A61B 5/14507 604/8 |
| 2014/0037656 A1* | 2/2014 | Felder | A61M 27/006 424/178.1 |
| 2014/0155816 A1* | 6/2014 | Cheng | A61P 43/00 604/28 |
| 2015/0094644 A1* | 4/2015 | Lenihan | A61M 27/006 604/9 |
| 2015/0136701 A1* | 5/2015 | Chait | A61M 1/3687 210/662 |
| 2017/0035950 A1* | 2/2017 | Meyering | A61M 1/0098 |
| 2017/0157374 A1* | 6/2017 | Hedstrom | A61M 27/006 |

* cited by examiner

APPARATUS AND METHOD FOR CEREBRAL MICRODIALYSIS TO TREAT NEUROLOGICAL DISEASE, INCLUDING ALZHEIMER'S, PARKINSON'S OR MULTIPLE SCLEROSIS

RELATED APPLICATIONS

This application is related to provisional patent application, entitled, Apparatus and Method for Cerebral Microdialysis to Treat Neurological Disease, Including Alzheimer's, Parkinson's or Multiple Sclerosis, Ser. No. 62/271,866, filed on Dec. 28, 2015 under 35 USC 119, which is incorporated herein by reference.

BACKGROUND

Field of the Technology

The invention relates to the field of methods and apparatus for the treatment of neurocognitive diseases and conditions of which Alzheimer's disease (Alzheimer's disease) and Parkinson's disease are examples.

Description of the Prior Art

Human CSF is a clear, colorless fluid produced in the choroid plexuses of the ventricles of the brain. It acts as a cushion or buffer for the brain's cortex, providing basic mechanical and immunological protection to the brain, and it also functions in the auto-regulation of cerebral blood flow. The CSF occupies the subarachnoid space and the ventricular system around and inside the brain and spinal cord making it accessible to antibody delivery and mechanical transport by an implantable pump with suitable catheter delivery system.

The prior art teaches diffusion cerebral micro-dialysis to monitor local tissue biochemistry. Diffusion cerebral microdialysis is performed by inserting a fine dual lumen catheter, lined at its tip with a semi-permeable dialysis membrane, into the brain tissue. The catheter is perfused via an inlet tube with a fluid isotonic to the tissue interstitum. The perfusate passes along the dialysis membrane before exiting the catheter via the second lumen into a collection chamber. A concentration gradient drives the passage of molecules across a dialysis membrane, so that molecules at higher concentration pass into the perfusate and thence into a collection chamber. Of note, diffusion cerebral micro-dialysis reflects only local tissue biochemistry, and the accurate placement of the catheter tip is essential. Nevertheless, there is a growing body of clinical evidence that local diffusion cerebral micro-dialysis could provide early warning of impending hypoxia/ischemia and neurological deterioration after acute brain injury. Comprehensive cerebral dialysis has not been addressed in medical practice.

Alzheimer's Disease and Other Dementias

Dementia represents a family of neurocognitive diseases and conditions of which Alzheimer's disease (Alzheimer's disease) and Parkinson's disease widely recognized. Clinically speaking, dementia is an overall term for diseases and conditions characterized by a decline in memory or other thinking skills that affect a person's ability to perform everyday activities. Several forms of dementia are caused by damage to nerve cells (neurons) in the brain by deposition of proteins either onto or within the neurons.

Millions of Americans presently suffer from Alzheimer's disease and other dementias. The Alzheimer's Association estimates 5.2 million Americans of all ages experienced Alzheimer's disease in 2014. Worldwide in 2015, nearly 44 million people are expected to have Alzheimer's disease or other related dementia. The number of people with Alzheimer's disease and other dementias is expected to grow each year as the size and proportion of the population age 65 and older continues to grow and the baby boom generation ages. As of 2014, a staggering 1 in 9 people age 65 and older suffered from Alzheimer's disease. Alzheimer's disease is listed as the sixth-leading cause of death in the USA, and it rises to the fifth-leading cause of death for those of age 65 or older.

Among the physiological changes contributing to the development of Alzheimer's disease is the accumulation of protein amyloid beta plaques outside of the neurons and an abnormal form of protein tau tangles inside the neurons. The accumulation of amyloid beta plaques from amyloid beta precursor protein (A$\beta$) interferes with the inter-neuron synapse communication process and culminates in neuron death. Tau tangles block the transport of nutrients and other essential molecules and hence further contribute to neural cell death. The brains of people with advanced Alzheimer's disease show dramatic shrinkage from cell loss and widespread debris from dead and dying neurons. A$\beta$ and tau protein are being actively investigated by the pharmaceutical industry as logical biological targets for therapeutic intervention.

Genetically, Alzheimer's disease is heterogeneous and complex, displaying no single or simple mode of inheritance. People with rare, early onset familial Alzheimer's disease express mutations of amyloid precursor protein or presenilin genes that culminate in the production and deposition of amplified amounts of Abeta peptide in the brain. Others have demonstrated that soluble CSF A$\beta$ can be measured on a dynamic time scale. The presence of such circulating proteins in the CSF across Alzheimer's disease patients, logically suggests protein removal from the CSF prior to deposition may help slow, or even reverse, the progression of Alzheimer's disease symptoms, and particularly if intervention occurs at an early stage of the disease.

Alzheimer's disease is presently treated by pharmacologic intervention and non-pharmacologic therapy. None of the pharmacologic treatments available today for Alzheimer's disease slow or stop the malfunction and death of neurons in the brain that cause dementia and eventually make the disease fatal. As of 2014, the US FDA had approved five Alzheimer's disease drugs that target increases in level of neurotransmitter chemicals within the brain. While these products may temporarily improve the symptoms of Alzheimer's disease; none offer a cure. Similarly, a wide range of non-pharmacological interventions have been proposed or studied, but to date only cognitive stimulation has findings that support a temporary beneficial effect.

Amyloid beta (A$\beta$ or Abeta) denotes peptides of 36-43 amino acids that are crucially involved in Alzheimer's disease as the main component of the amyloid plaques found in the brains of Alzheimer patients. The peptides result from the amyloid precursor protein (APP), which is cleaved by beta secretase and gamma secretase to yield A$\beta$. A$\beta$ molecules can aggregate to form flexible soluble oligomers which may exist in several forms. It is now believed that certain misfolded oligomers (known as "seeds") can induce other A$\beta$ molecules to also take the misfolded oligomeric form, leading to a chain reaction akin to a prion infection. The seeds or the resulting amyloid plaques are toxic to nerve cells. The other protein implicated in Alzheimer's disease, tau protein, also forms such prion-like misfolded oligomers, and there is some evidence that misfolded Aβ can induce tau to misfold. It is believed that the Aβ cascade is initiated by an elevated Aβ concentration, in particular $A\beta_{42}$, which aggregates to form soluble dimers, trimers, and low-ordered oligomers. Further aggregation leads to insoluble and proteolysis-resistant fibrils, which accumulate as protein deposits. This toxic Aβ cascade is associated with various neuropathological processes that culminate in the progressive loss of neuronal function.

Over the past decade, the study of Aβ immunotherapy has rapidly progressed. The accompanying Table 1 highlights some Aβ antibodies that have entered clinical trial development. Recently, Biogen's Aducanumab, is a high affinity, humanized monoclonal antibody (mAb) against a conformational epitope found on Aβ, and has gained FDA approval to directly advance from Phase I into Phase III clinical development. Biogen has announced that Aducanumab dose-dependently reduces amyloid deposition in 6 cortical regions of the brain. In comparison to the Aβ antibodies in development for disease modification of Alzheimer's disease, immunotherapies for circulating tau protein are not nearly as well advanced.

Animal studies suggest peripherally administered antibodies can enter the central nervous system (CNS) and bind to Aβ, wherein the antibody-Aβ complex is eliminated via the Fc receptor-mediated clearance pathway of microglial cells. However, the concentration of the Aβ antibodies in the brain parenchyma only reaches 0.1% of that in serum because of the low passage of antibodies across the blood-brain-barrier (BBB). These same antibodies have to pass through further barriers to reach intracellular compartments of the brain. Consequently, intraneuronal antibody concentrations may not be sufficient to reduce intracellular Aβ levels, impacting clinical efficacy and compounding the challenges of achieving a therapeutically effective dose at the target site.

A major pathological hallmark of Alzheimer's disease (AD) is the formation of neuritic plaques within the gray matter of AD patients. These plaques are composed primarily of filamentous aggregates (fibrils) of the 39- to 42-residue-long amyloid-β (Aβ) peptide formed from the proteolytic cleavage of the amyloid precursor protein by β- and γ-secretases. The major species in Aβ production are the Aβ40 and Aβ42 peptides, with Aβ42 being predominant in neuritic plaques of AD patients and showing a higher in vitro propensity to aggregate and form amyloid fibrils. Familial AD mutations result in an increase in the Aβ42:Aβ40 ratio in cell culture and mouse models, and elevated plasma levels of Aβ42 seem to be correlated with AD11. Given the pathological significance of the Aβ42 peptide, determining the molecular structure of its fibrils and prefibrillar oligomers is crucial for elucidating the aggregation pathway involved in plaque formation and for developing therapeutic and diagnostic agents.

This application incorporates by reference U.S. Pat. No. 8,323,270, "Enhanced Method For Delivering Bevacizumab (Avastin) Into A Brain Tumor Using An Implanted Magnetic Breather Pump", and U.S. Pat. No. 8,323,269, "Metronomic Convection Enhanced Delivery Of Intrathecal Chemotherapy Using".

What is needed is a better way to remove Aβ antibodies.

BRIEF SUMMARY

The illustrated embodiments of the invention include a medical device and method for cerebral micro-dialysis to treat neurological disease, including Alzheimer's, Parkinson's or multiple sclerosis. These devices function by mechanical transport of a patient's cerebrospinal fluid (CSF), which contains diseased cells or biomolecules associated with the neurological disease, to a separation apparatus wherein the diseased cells or biomolecules are removed. A pump within the device mechanically transports the CSF to the separation apparatus. The separation apparatus includes a dialysis membrane or filter impregnated with an antibody, a reversible electrostatic filter, and/or a magnetic field effect fractionation chamber wherein magnetically-tagged antibodies scavenge and aid in the removal of circulating diseased cells or biomolecules from the CSF.

The present invention for cerebral micro-dialysis differs from the prior art in the following important ways: (1) a pump within the device mechanically transports circulating CSF to a separation apparatus for separation of diseased cells or biomolecules, (2) the separation apparatus may comprise a porous membrane or filter, or a reversible electrostatic filter, and/or a magnetic field effect fractionation chamber, and (3) a molecular recognition agent (i.e., an antibody) having high binding affinity and specificity toward the diseased cells or biomolecules in the CSF may aid the efficiency of separation process.

The illustrated embodiments of the invention provide highly efficient methods for cerebral micro-dialysis of body fluid in the treatment of neurological disease.

In one embodiment, an implantable device is used to deliver a molecular recognition agent to a patient's biological fluid and remove a diseased associated antigen from the biological fluid by means of the formation of a molecular recognition agent-antigen complex.

In an embodiment, the biological fluid is the CSF.

In an embodiment, the molecular recognition agent is an antibody, an aptamer or an oligomer.

In another embodiment, the molecular recognition agent is a humanized monoclonal antibody having high specificity and selectivity for the disease-associated antigen.

In another embodiment, the antigen is a protein or cell associated with the underlying disease.

In yet another embodiment, the antigen is Aβ or tau protein.

In another embodiment, the molecular recognition agent-antigen complex is an antibody-protein complex, an antibody-diseased cell complex, an aptamer-biomolecules complex, or an oligonucleotide-biomolecules complex.

In yet another embodiment, the molecular recognition agent-antigen complex is a humanized monoclonal antibody-protein complex.

In still yet another embodiment, the molecular recognition agent-antigen complex is a humanized monoclonal antibody-Aβ protein complex or a humanized monoclonal antibody-tau protein complex.

In another embodiment, a MP is attached to the antibody, or the magnetic particle is optionally attached to the antibody through a LINK, to produce a magnetic particle-tagged antibody.

In another embodiment, the magnetic particle is an iron nanoparticle or other non-toxic magnetic material.

In still another embodiment, the magnetic particle is a bacterial magnetic particle.

In yet another embodiment, the magnetic particle-tagged antibody has specificity and selectivity for the disease-associated antigen.

In still another embodiment, the magnetic particle-tagged antibody exhibits minimal toxicity or adverse effect in humans.

In another embodiment, the magnetic particle-tagged antibody is stored in and delivered to a patient's biological fluid from the antibody storage reservoir.

In an embodiment, the antibody storage reservoir is located internal of the device or in a shunt connecting the device to the catheter tip. In medicine, a shunt is a hole or a small passage which moves, or allows movement of, fluid from one part of the body to another. Cerebral shunts are used in cases of hydrocephalus and other conditions that cause chronic increased intracranial pressure, as a one-way valve to drain excess cerebrospinal fluid from the brain and carry it to other parts of the body. This valve usually sits outside the skull, but beneath the skin, somewhere behind the ear.

In still yet another embodiment, the dual lumen catheter routes flow of the magnetic particle-tagged antibody from the ASR into a patient's biological fluid.

In an embodiment, a magnetic particle-tagged antibody-antigen complex is established in vivo when the magnetic particle-tagged antibody encounters a disease-associated antigen circulating in the biological fluid.

In another embodiment, the magnetic particle-tagged antibody-antigen complex is routed to the device via the dual lumen catheter.

In yet another embodiment, the magnetic particle-tagged antibody-antigen complex is magnetic field effect fractionated within the magnetic capture reservoir.

In another embodiment, the magnetic capture reservoir has a magnetic surface.

In still another embodiment, the magnetic surface in the magnetic capture reservoid is an electromagnet.

In another embodiment, cleansed biological fluid is returned to the patient so as establish a loop dialysis system.

In yet another embodiment, the cleansed biological fluid is returned from the magnetic capture reservoir via the dual lumen catheter to the subarachnoid space of the cranium or into the patient's abdomen.

In another embodiment, the molecular recognition agent is impregnated on a membrane or filter to produce an Impregnated membrane or filter.

In another embodiment, the impregnated membrane or filter is impregnated with an antibody, an aptamer or an oligonucleotide.

In still another embodiment, the impregnated membrane or filter is impregnated with a monoclonal antibody to $A\beta$ or tau protein.

In another embodiment, the impregnated membrane or filter is engaged in a cartridge.

In still another embodiment, the cartridge is placed internal of the device or within a shunt.

In yet another embodiment the invention, the cartridge contains multiple units of the impregnated membrane or filter.

In another embodiment, one lumen of the dual lumen catheter draws the CSF to the impregnated membrane or filter wherein the $A\beta$ or tau protein binds to the impregnated antibody on the membrane or filter.

In another embodiment, cleansed CSF is discharged via another lumen of the catheter to the subarachnoid space of the cranium or into the patient's abdomen.

In an embodiment, a reversible electrostatic filter is used to capture circulating antigen from the CSF.

In an embodiment, the circulating antigen is a protein has a natural positive charge.

In another embodiment, the reversible electrostatic filter is given a negative charge.

In another embodiment the invention, one lumen of the dual lumen catheter draws the CSF to the reversible electrostatic filter.

In yet another embodiment the protein having a natural positive charge is attracted to and held by the reversible electrostatic filter given a negative charge.

In another embodiment, cleansed CSF is discharged via another lumen of the dual lumen catheter to the subarachnoid space of the cranium or into the patient's abdomen.

In still yet another embodiment, the charge of the reversible electrostatic filter is reversed to a positive charge, release the protein from the reversible electrostatic filter.

In an embodiment, an optional biosensor delivers biofeedback regarding disease progression and regression.

In another embodiment, the optional biosensor detects monitors levels of a disease-associated antigen present in the patient's biological fluid.

In an embodiment, the optional biosensor is a standalone, companion device to the cerebral microdialysis device.

In yet another embodiment, the optional biosensor is internal to the cerebral microdialysis device.

In yet another embodiment, the disease-associated antigen is $A\beta$ or tau protein.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 6 is a schematic of the magnetic field effect fractionation device. The following descriptors are used herein to describe the embodiments of the invention: amyloid beta ($A\beta$), MBP antibody storage reservoir (ASR), dual lumen catheter (DLC), humanized $A\beta$ monoclonal antibody (mAb), optional monoclonal antibody linker (LINK), magnetic particle (MP) and MBP magnetic capture reservoir (MCR).

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
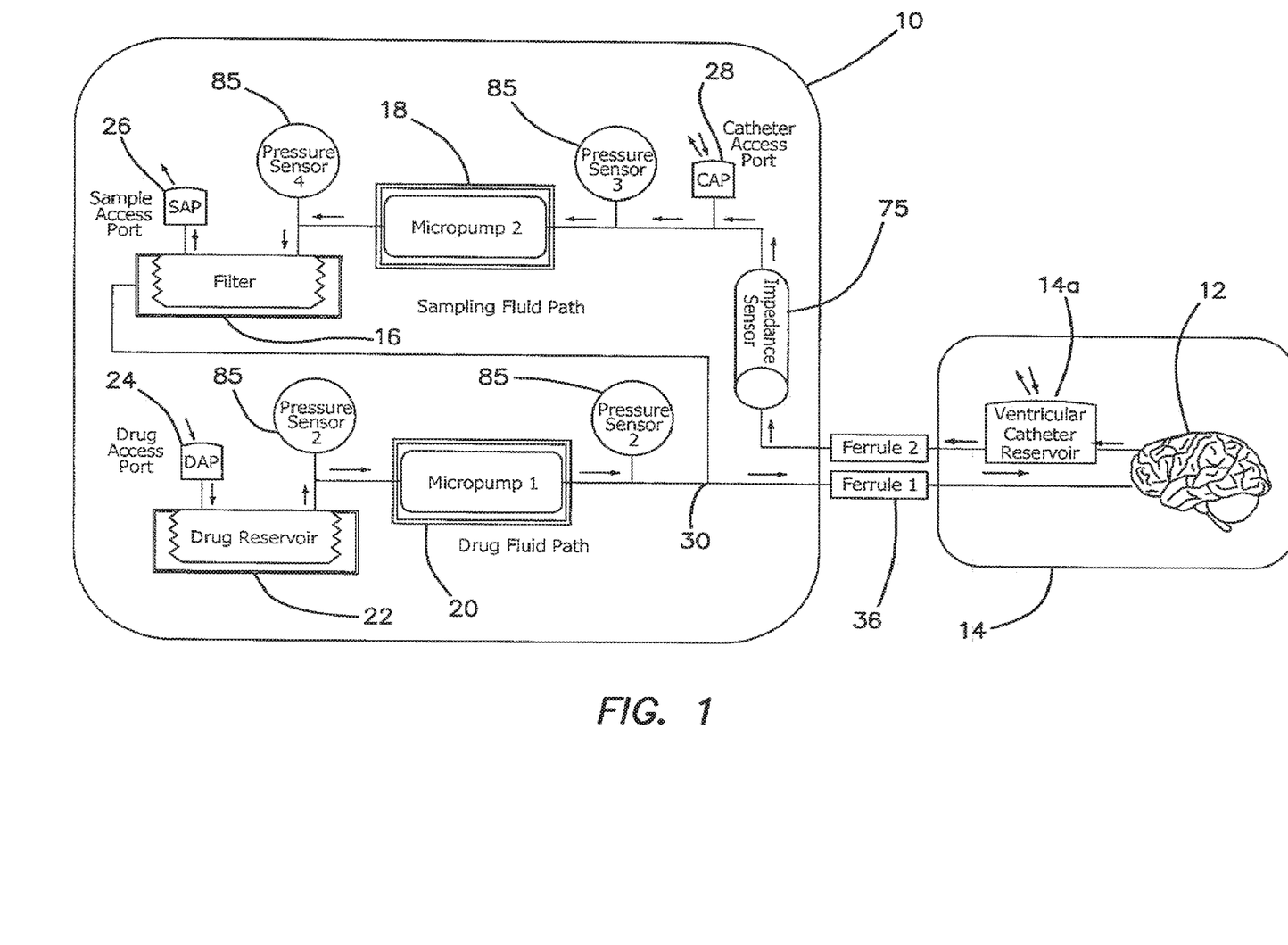
FIG. 1 is a schematic diagram of the primary elements of the dialysis pump as applied to Alzheimer's disease.

FIG. 1 is a schematic diagram of an implantable Alzheimer's disease (AD) microdialysis device 10 using a dual lumen catheter 14 to treat a brain 12 by application of medication and CSF to brain 12. CSF is drawn in a conventional manner from brain 12 into catheter 14 to a filter 16 by CSF circulation pump 18. Filter 16 includes a backwash inlet port 28 and outlet port 26. Medication pump 20 draws a medication from reservoir 22 and feed it to a T intersection 30 where is it combined with re-circulated CSF from pump 18 through a recirculation line not shown in FIG. 1, but seen in FIG. 4. Reservoir 22 is filled through medication fill port 24. The mixed CSF and medication is then supplied through catheter 14 to brain 12.

Figure 2:
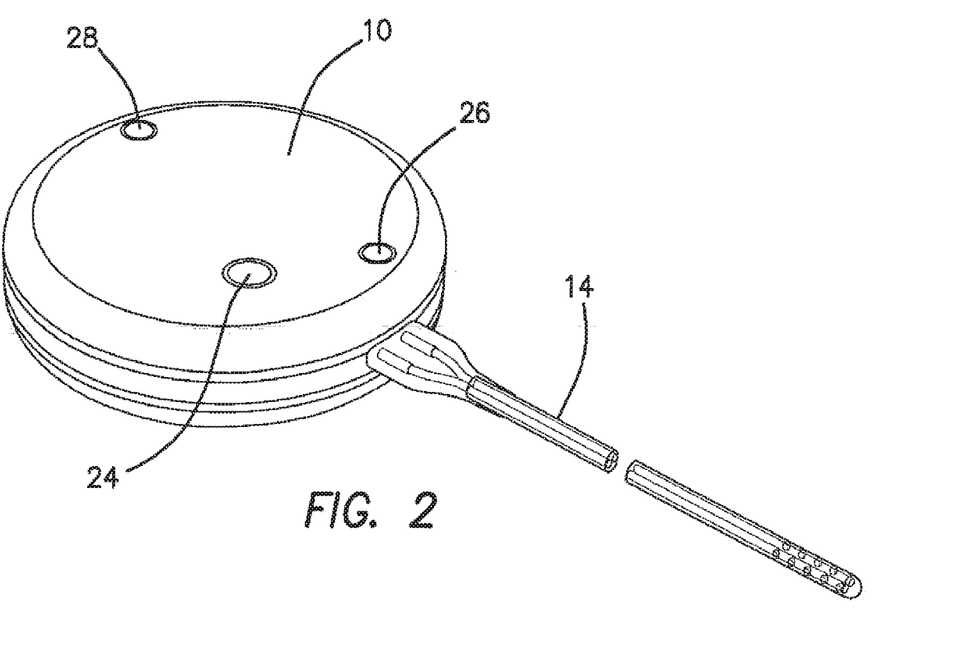
FIG. 2 is a perspective view of the exterior of device 10 showing its coupling to catheter 14 and the filter backwash ports 26, 28 and medication fill port 24.

FIG. 2 is a perspective view of the exterior perfusion pump device 10 showing its coupling to catheter 14 and the exterior self-sealing membranes covering outlet port 26, filter backwash port 28 and medication fill port 24.

Figure 3:
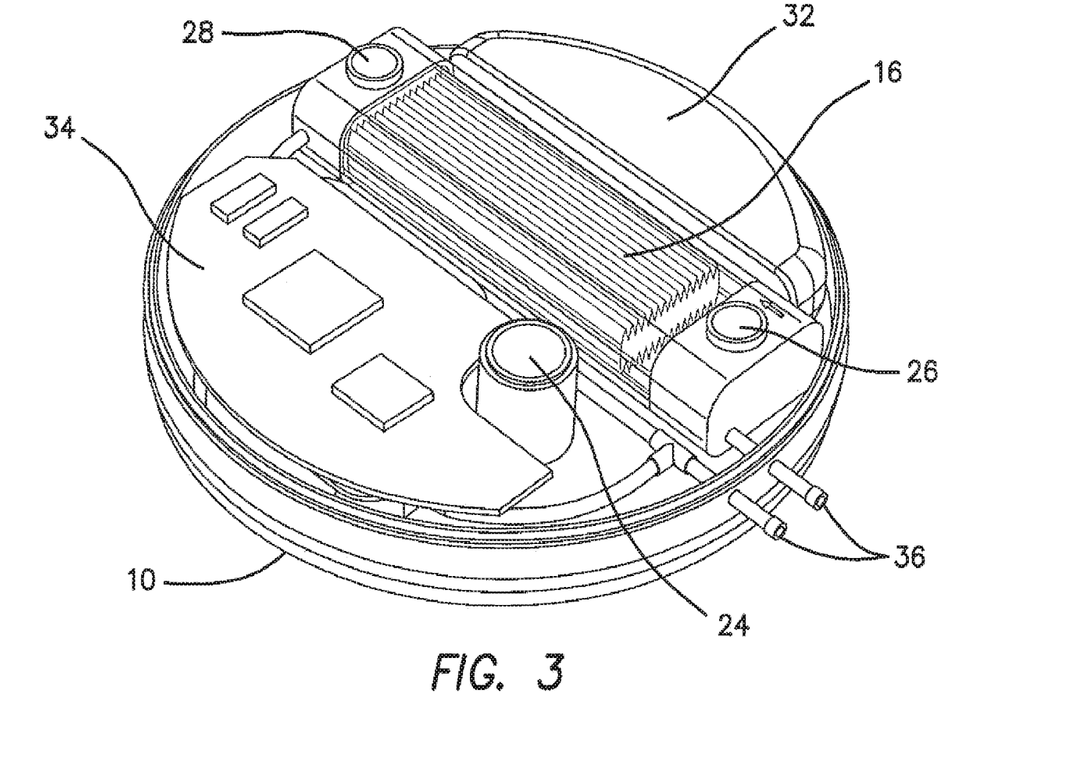
FIG. 3 is a perspective view of the microdialysis device with its top cover removed.

FIG. 3 is a perspective view of device 10 with its top cover removed revealing the battery 32 which powers device 10 and printed circuit board 34 which carries multiple integrated circuits for the control and monitoring functions of device 10. Dual catheter ports 36 are shown extending through the side of device 10 for the input and output of CSF and CSF/medication respectively. The tee connection 30 to catheter port 36 for recirculation of CSF is clearly depicted.

Figure 4:
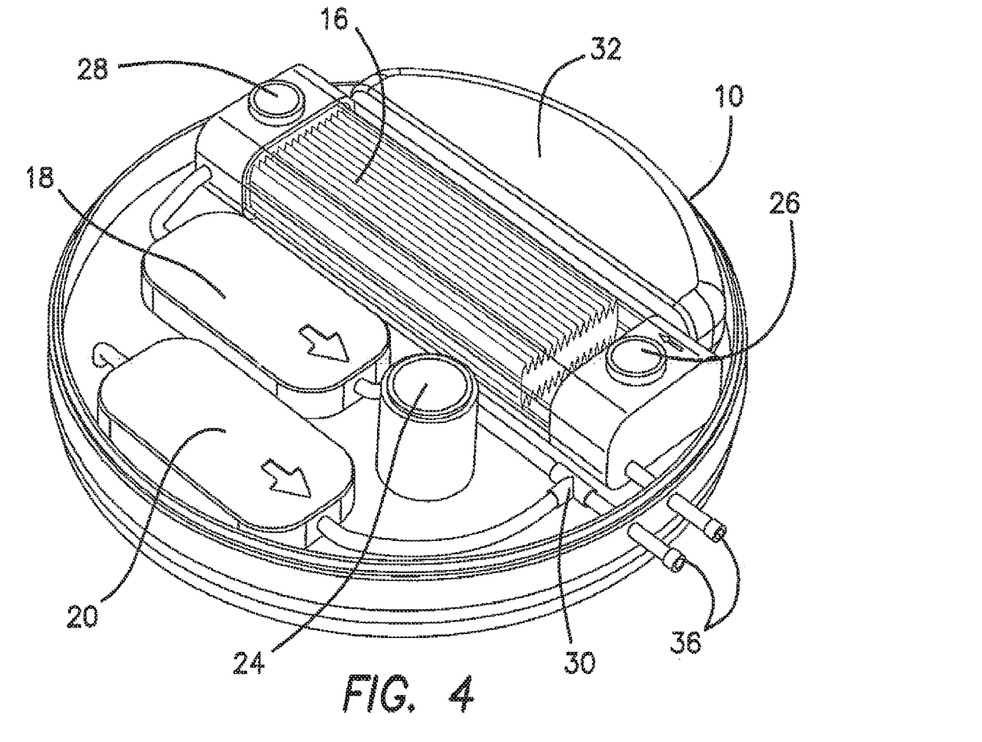
FIG. 4 is a perspective view of the microdialysis device in the view of FIG. 3 with the printed circuit board removed.

FIG. 4 is a perspective view of another embodiment of device 10 in the view of FIG. 3 with the printed circuit board 34 removed to show the underlying circulation pump 18 and medication pump 20. Medication reservoir 22 is placed below pumps 18 and 20 and is therefore concealed from view in FIG. 4 as well as the interconnections with port 24 and pump 20. Several differences from the device organization shown in FIG. 4 from that of FIG. 1 is evident. In the embodiment of FIG. 4 pump 18 is downstream from filter 16 and filter 16 is directly coupled to ferrule 36.

Figure 5:
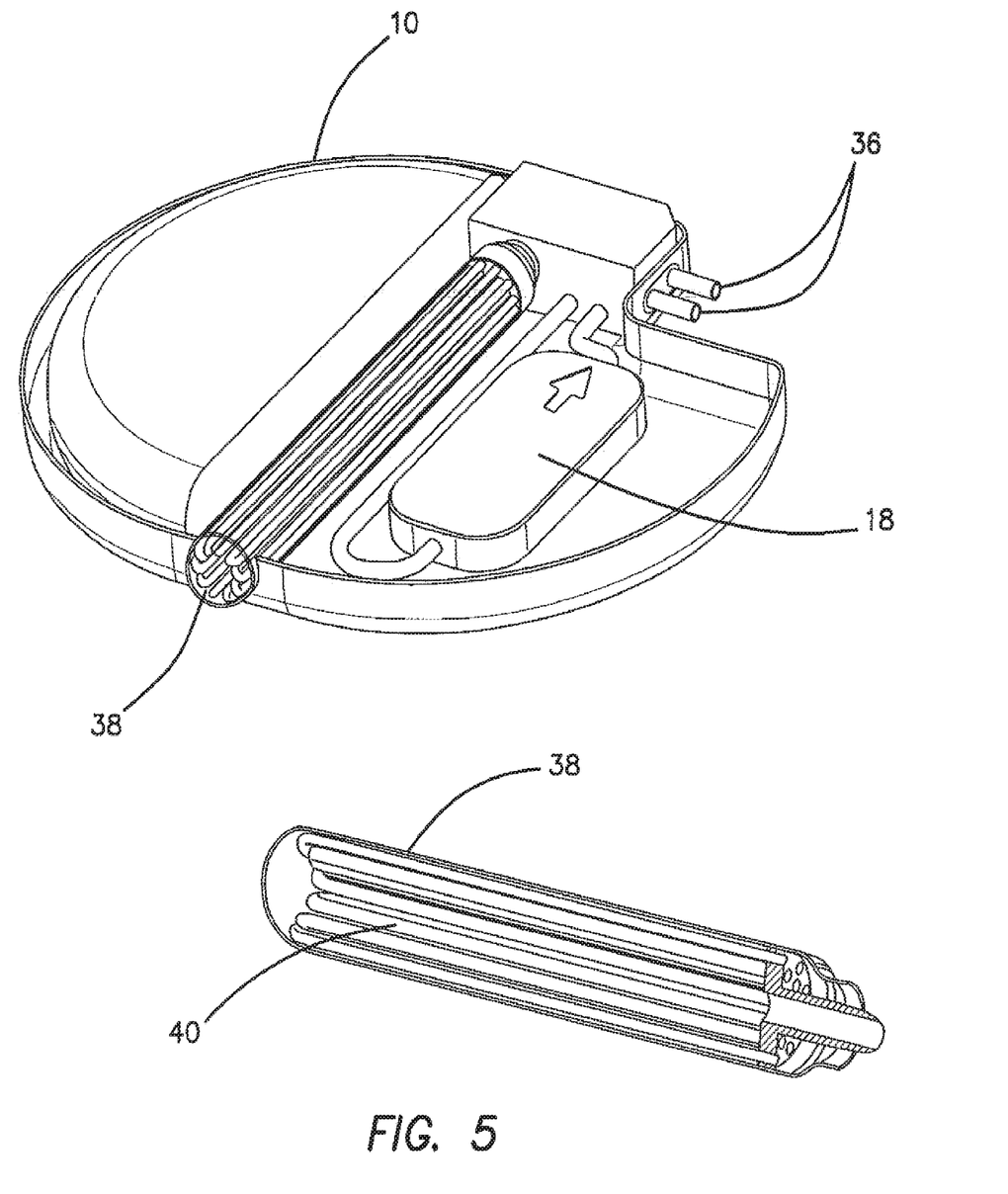
FIG. 5 is a perspective view of another embodiment of the microdialysis device where a cylindrical, replaceable membrane filter cartridge is used.

FIG. 5 is a perspective view of another embodiment of device 10 where a cylindrical, replaceable membrane filter cartridge 38 with filter elements 40 is used in place of the filter 16. Other elements of device 10 have been removed from the illustration for the sake of simplicity of visualization.

Figure 5A:
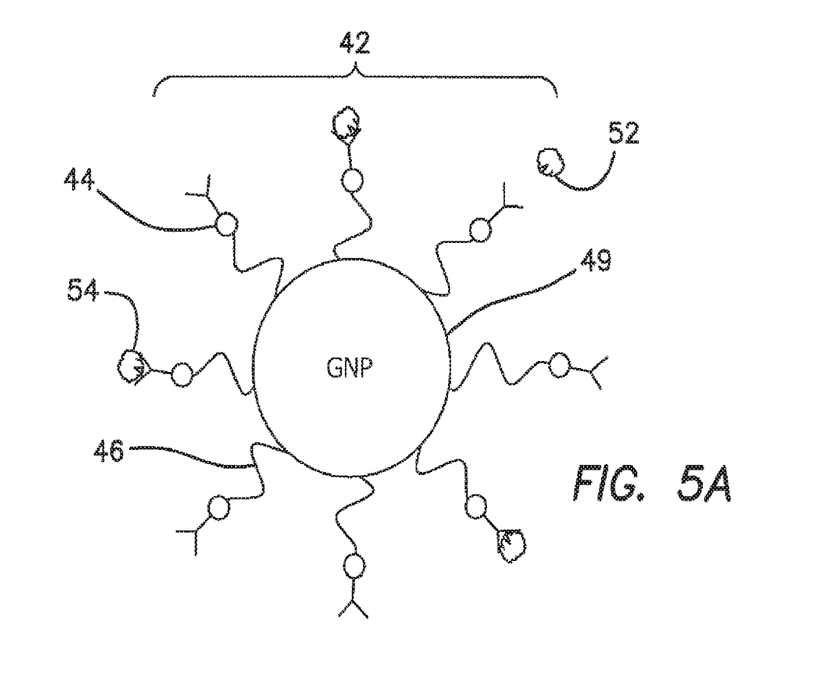
FIG. 5A is an orthographic representation of a gold nanoparticle (GNP) functionalized with probes.

FIG. 5A is an orthographic representation of a gold nanoparticle (GNP) 49 from 1 nm to 30 nm in diameter, functionalized with probes 44, either protein-specific aptamer or antibody, bound to its surface by a linker molecule 46. Probes 44 capture analyte 54.

Figure 5B:
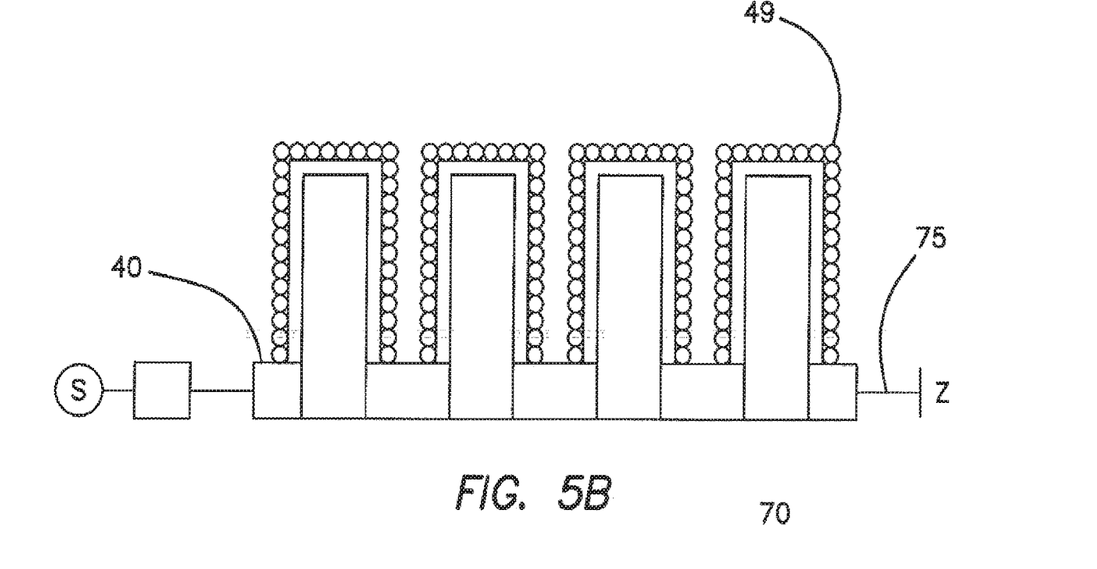
FIG. 5B is a detailed representation of the optional filter cartridge geometry.

FIG. 5B is a detailed representation of the optional filter cartridge element 40 whereby a substrate 70 such as $SiO_2$ forms the bonding layer for the GNP 49 coating to which the antibody or aptamer capture probes 44 are bound by the linker molecules 46 of FIG. 5A. The impedance sensor 75 shown in FIG. 1 of the cartridge 38 measures the saturation level of captured analyte 54 with which the impedance sensor 75 is loaded.

Figure 6:
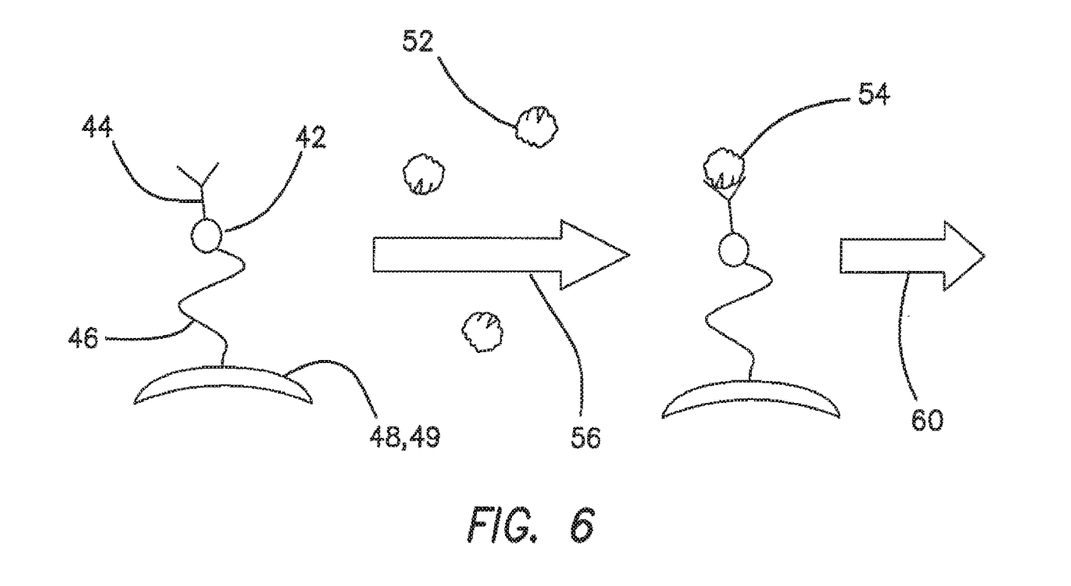

FIG. 6 is a graphic representation of the complex capture probe 42 with GNP 49 or magnetic beads 48, the linker 46 and antibody or aptamer probes 44 forming the complex unit 42. CSF containing the circulating analyte (e.g. the Aβ protein) 52 is retrieved via catheter step 56, and captured by the probe in the binding step 54, thereby increasing the load on the filter cartridge 38, resulting in reduction of the undesired biological payload within the analyte portion.

In one embodiment, the circulating CSF is further disposed by transferring the remaining CSF at step 60 through a catheter to the peritoneum for discharge through the urinary system.

Consider now a more detailed description of the AD microdialysis device 10 and its operation as follows. The device 10 is cranially implanted in one embodiment. The microdialysis implant 10 includes three parts: a ventricular catheter reservoir 14 (double lumen), pump tubing 36, and a pump 18 which contains the dialysis membrane 16. The ventricular catheter reservoir 14 is inserted into the right frontal horn of the lateral ventricle. The ventricular catheter reservoir 14 is one piece and is anchored to the periosteum of the skull, with a port allowed for CSF sampling. It is connected to the pump tubing 36 which is also double lumen, and connected to the pump itself 18. The pump is Wifi-controlled externally and has a flow sensor and pressure sensor 85. It is passed onto a filter membrane 16, and the cleaned CSF is returned back to the pump tubing 36 back into the ventricles. The device 10 is placed above the pectoralis muscle of the chest.

In another embodiment the device is alternatively implanted in the lumbar space. The microdialysis implant includes four parts (FIG. 1): intrathecal catheter 14, reservoir 14a (collectively denoted as 14 in FIG. 1), pump tubing 36, pump 18 with filter membrane 16. The intrathecal catheter goes into the lumbar Dural sac (L3-4, L4-5, or L5-S1). It is double lumen and connected to a reservoir 14a anchored to the side of the side of the patient (detailed anatomical representation is avoided for clarity). The reservoir 14a allows CSF to be sampled. The pump tubing 36 is connected to the reservoir 14a and is connected to the pump 18 (containing the filter membrane 16, flow sensor, and pressure sensor 85) which is placed above the lumbar fascia. The pump is wifi controlled and is able to turn on the fluid circulation at maintained schedules. CSF will be returned back to the thecal sac after it is filtered by the filter membrane.

In the illustrated embodiments three complementary adaptations of the metronomic biofeedback pump (MBP) 10 of Cognos Therapeutics Inc. are addressed. These adaptations are directed to the extraction of circulating Aβ from the CSF of Alzheimer's disease patients (i.e., cerebral microdialysis of the CSF). Each adaptation incorporates a separation apparatus including of one of the following:

(a) a dialysis member or filter 16 containing impregnated antibodies (i.e., the molecular recognition agent) to Aβ protein;

(b) a reversible electrostatic filter 16 that is able to bind positively-charged Aβ protein, and which filter 16 can be later charged reversed to release the bound protein; and/or (c) a separation chamber included within filter 16 wherein a magnetically-charged antibody to Aβ is removed from the CSF via magnetic field effect fractionation.

(d) A filter cartridge 38 containing a surface 40 whereby antibodies 44 for the purpose of conjugating the analyte, for example such as Amyloid-Beta or Tau protein, is functionalized with capture probes 42 linked to gold nanoparticles 49 via linker molecules 46 to form a complex probe with affinity for recovery of the analyte 52 of interest.

Figure 7:
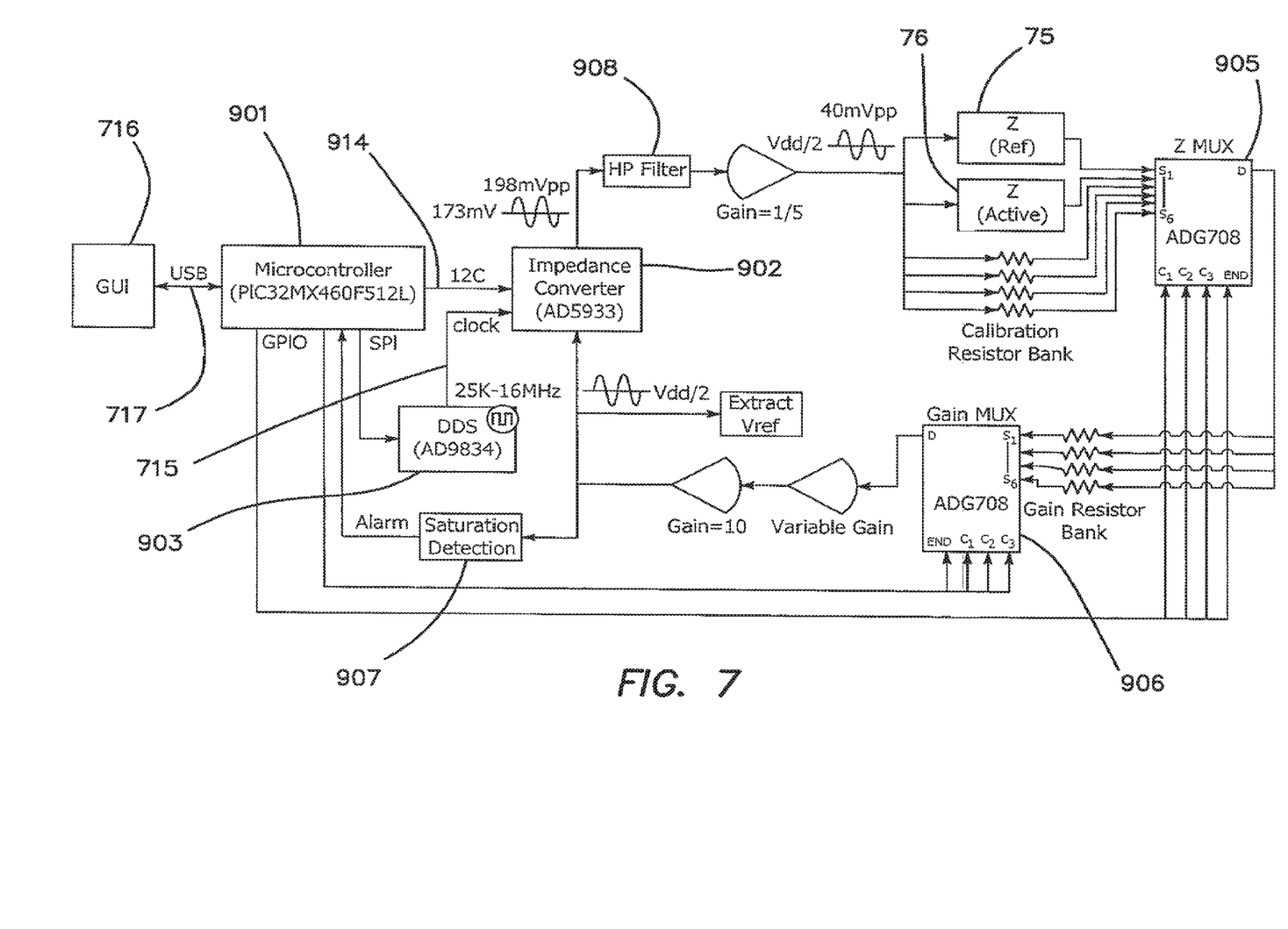
FIG. 7 is a block diagram of the impedance detection circuit identifying saturation of the filter cartridge.
Figure 7A:
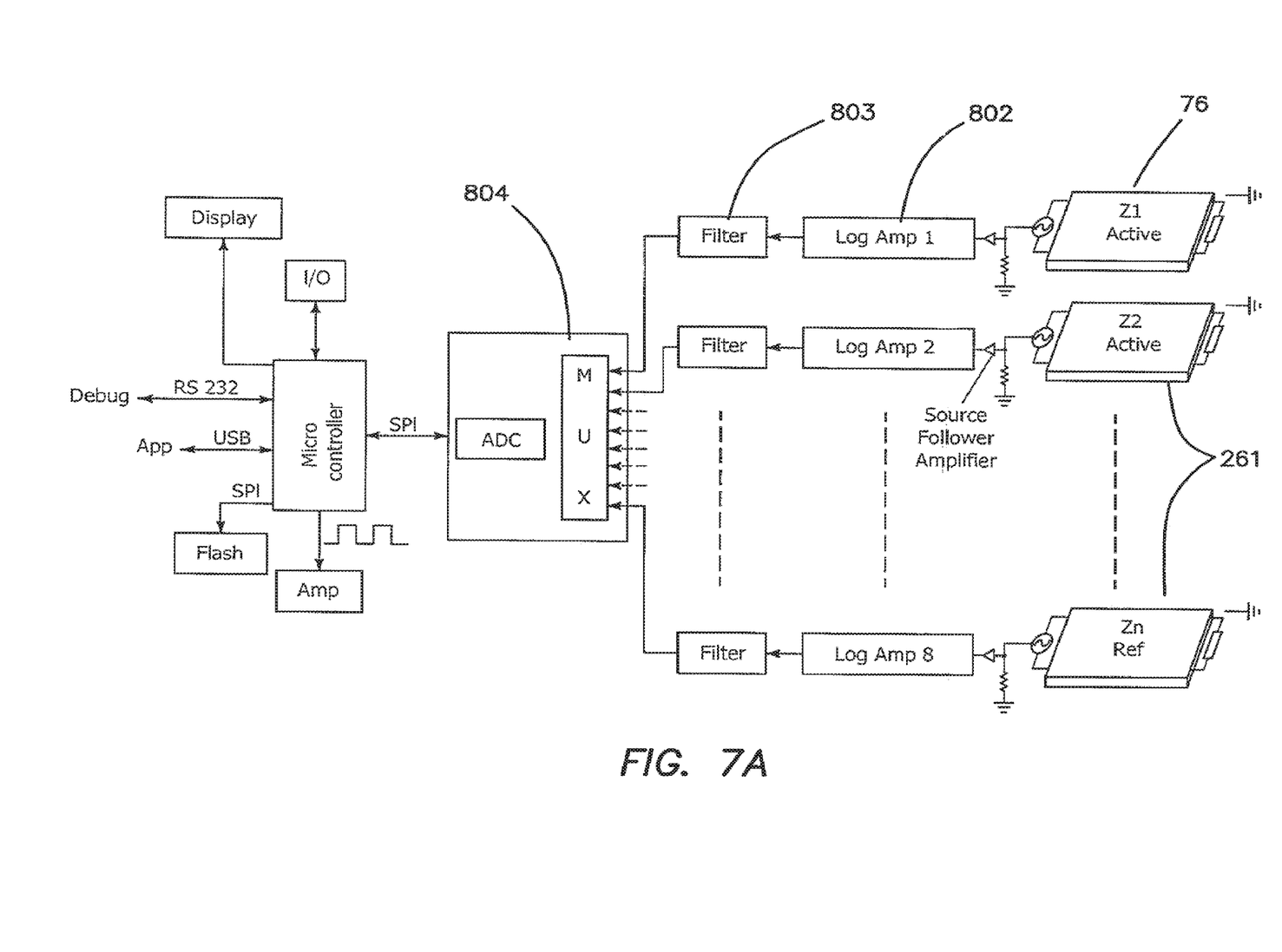
FIG. 7A is a block diagram of a pathfinder/reader describing the analog front end coupled to the array of cells that are multiplexed and digitized into its microcontroller.

What is indicated as impedance sensor 75 in FIG. 1 may include the circuitry of FIGS. 7 and 7A. The circuitry of FIGS. 7 and 7A is similar to those described in U.S. patent application Ser. No. 14/625,445 and U.S. Provisional Patent Application Ser. No. 62/397,233, incorporated herein by reference. FIG. 7 is a block diagram of the electronic circuit, which detects hybridization of the analyte e.g., in serum, CSF employing the sensors 75, 76 after appropriate surface modification of the sensing element on the basis of application on hand. In the embodiment of FIG. 7 a time dependent measurement of the saturation of the sensor cell 75 is used as the data point. A microcontroller 901 coupled to an impedance converter 902, a direct digital synthesizer (DDS) 903, and a Z multiplexer (MUX) 905 is included. Z multiplexer (MUX) 905 has its output coupled to a gain multiplexer (MUX) 906, and in turn to a saturation detection circuit 907 feeding back an alarm signal to the microcontroller 901. Impedance converter 902 is coupled to high pass filter 908 and to an amplifier whose output is coupled to active and reference impedance sensors 76 and 75 respectively. The circuit of FIG. 7 operates with a sweep frequency of 50 Hz to 100 kHz. In one embodiment the sweep frequency is capable of going lower than 50 Hz with impedance range of 50Ω to 10 MO, providing for example 16 sweep points to define the linear response curve. It is within the spirit and scope of the invention to increase the number of sweep points to augment the number of data points and to further improve the statistics so as to represent a smoother linear curve. The circuit of FIG. 7 also includes additional mathematical signal processing tools within the microprocessor e.g. using a least squares or the polynomial curve fitting algorithm by the Newton-Raphson method.

The circuit of FIG. 7 is a multiplexed data acquisition and analysis platform for measuring and recording of hybridization and flow cytometric analysis of analyte-antibodies in assays that perform simultaneous measurement of multiply different analytes. The system 10 includes a filter cartridge 38 with a distinct sets of specific probes and the resultant output of the hybridizations are addressable by the resident microcontroller 901 interfaced with a digital signal processing board and software. In one embodiment, we employ individual sets of microspheres such as gold nanoparticles (GNPs) 49 which can be modified with reactive components such as antigens, antibodies, or oligonucleotides, and then mixed to form a multiplexed assay set. The digital signal-processing hardware and software provide complete control of the flow cytometer and perform real-time data processing, allowing multiply independent reactions to be analyzed simultaneously. The circuit of FIG. 7 performs qualitative and quantitative immunoassays for multiple serum proteins. The system can be used to perform DNA sequence analysis by multiplexed competitive hybridization with different sequence-specific oligonucleotide probes.

FIG. 7A is a block diagram of the saturation detection circuit comprising the impedance detector 76 with its reference unit, using a signal transduction by a scaling log amplifier 802 and filters 803, thereby multiplexed for the specific filter cartridge containing the analyte with the specific antibody hybridization probe, which thereby counts the amount of specific analyte binding onto the available antibody located on the surface of the filter element 40. The purpose of such detector modality is to enable a physical count as well as saturation of the filter cartridge to enable monitoring of the process of collecting the analyte and reporting.

The purpose of such circuitry and its embodiment is to enable the user to replace the filter cartridge 38 from time to time.

The circuit architecture schematically depicted in FIG. 7A comprises of the analog interface 802 and digital processing unit 804. The source follower amplifier of each filter cell is coupled to a corresponding log amplifier 802. The use of logarithmic analog computational method is employed by to widen the dynamic range of impedance input value generated from the cartridge based on its dynamic hybridization of the analyte in question, such as the amyloid-beta or tau proteins.

Logarithmic transduction affords advantages such as constant-precision sensing at any intensity (Weber's law) and is a requirement in designing circuit depicted by FIG. 7. If the concentration of a hybridization factor is fixed, and as the analyte conjugation increases in value, it is eventually binds all the available antibodies molecules and saturates the number of bound antibody/analyte complexes available. In addition, if the number of binding sites for a complex is limited (due to the finite cells of filter cartridge 38 and its sensor array 261 with their effective binding sites), these sites will eventually all be bound by available antibodies that saturate the cartridge surface. These two sources of saturation limit the dynamic range of hybridization and recording available. FIG. 7A shows a circuit approach that simultaneously alleviates both these saturation problems to widen the dynamic range. A filter 803 is then coupled to the output of each log amplifier 802 for the purpose of noise filtration. A multiplexer 804 multiplexes the analog outputs of the plurality of filtered log amplifiers and digitizes the analog signals in an included analog-to-digital converter. The data is then coupled to microcontroller 901 with a plurality of conventional input/output peripherals for data processing and display.

Consider now the overall use of device 10 and its various embodiments. The clinical advancement of Alzheimer's disease symptoms in a patient typically parallels that of increased neuron death. For this reason, the MBP could serve as an implantable cerebral microdialysis device 10 for treatment of dementia disease and provide the patient an extended quality of life (i.e., a quality of life extender but not a disease cure). More specifically, one embodiment includes a clinical method for slowing the progression of dementia by delivering targeted antibodies directly to the brain and removing circulating protein from the CSF before it deposits on the neuron. Even more specifically, the one embodiment includes a treatment of Alzheimer's disease by removing circulating Aβ protein from the CSF.

Another embodiment is directed to localized delivery of other antibody therapies, the removal of circulating tau protein from Alzheimer's disease patients, and treatment of other neurological diseases wherein biomolecules or diseased cells are circulating in the CSF. Representative examples of the latter include, but are not limited to, Parkinson's disease wherein protein alpha-synuclein aggregates appear in the brain, and multiple sclerosis wherein integrin alpha4 mediates organ-specific migration of immune cells to the inflamed brain. Moreover, the scope of the embodiments includes the use of other molecular recognition agents (i.e. aptamers and oligonucleotides). The specific Alzheimer's disease application discussed here is a matter of convenience only and is not intended to limit or restrict the scope of the embodiments.

Turn first to the dialysis membrane or filter separation apparatus 16. The use of the MBP pumping system as device 10 to capture and remove circulating Aβ protein from the CSF is by means of an antibody impregnated dialysis membrane or filter 16. Aβ antibodies are impregnated in the dialysis membrane or filter 16. The dialysis membrane or filter is engaged in a cartridge 38 in FIG. 5, which in turn is placed into the MBP pump system. The MBP catheter 14 has two lumens. The input lumen draws CSF into the separation apparatus 16 of the MBP pumping system or device 10, and the output lumen routes cleansed CSF back to the subarachnoid space of the cranium or into the patient's abdomen. Upon entering the separation apparatus 16, circulating Aβ protein binds to the impregnated antibody on the dialysis membrane or filter surface 40 and thereby is removed from the circulating CSF.

In practice a patient is treated periodically so that CSF is brought into contact with the membrane or filter 40 approximately once a week. At the end of a use cycle, and where the impedance detector indicates saturation of the cartridge, the saturated filter cartridge 38 is sequestered and replaced with the next section of the cartridge, and a new filter placed into its spot as shown in FIG. 5. Many variations of the filter replacement may be implemented. In one embodiment, the additional filter exposed to the analyte by sequential opening of available filter cells. The antibody for this device can be selected and licensed, for example, to any of the antibodies listed in Table 1. Because the total level of Aβ protein accumulates over extended periods of time, usually years, and baseline CSF concentrations of circulating Aβ are low (200-400 ng/mL), and the susceptibility for such a membrane or filter 40 to clog is minimized.

Turn now to the embodiment using a reversible electrostatic filter separation apparatus in place of hybridized filter 16, both of which shall be denoted as filter 16 hereinafter. A second mode of use of the MBP pumping system to capture and remove circulating Aβ protein from the CSF is by means of a reversible electrostatic filter 16. In this embodiment an electrostatic charge is the basis for affinity of the circulating biomolecules and not an antibody. Advantage is taken of the natural, positive electrostatic charge of Aβ protein. The reversible electrostatic filter in the separation apparatus 16 is initially negatively charged at a level sufficient to allow circulating Aβ to adhere to the surface of the filter 40 as CSF passes through it. After the CSF is cleansed, the filter 40 is reversed to a positive charge through a wireless controller, at which time the Aβ protein no longer adheres to the filter 40, and is captured in a compartment in the MBP pumping system (not shown). Once again, the input lumen of the MBP catheter 14 draws the CSF into the separation apparatus 16, and the output lumen routes it into the subarachnoid space of the cranium or into the patient's abdomen.

Third, turn to consider the use of a magnetic field effect fractionation separation apparatus denoted in this embodiment as filter 16. In this embodiment the MBP pumping system captures and removes circulating Aβ protein from the CSF by means of magnetic extraction of a functionalized antibody-Aβ complex 42 including the Aβ antibody 44, a link 46 and a magnetic tag 48 or gold nanoparticle (GNP) 49 illustrated in FIG. 6. This embodiment alternatively exploits the high affinity of an antibody for Aβ protein 44 and the principal of magnetic field effect fractionation to separate the magnetically-tagged antibody-protein complex 42 from the CSF. Such fractionation device comprises a dual reservoir MBP pumping system as shown in FIG. 1, delivery of a functionalized antibody 42 as a medication into the patient's CSF via one lumen of the catheter 14 in step 50, in vivo binding of the magnetically-tagged antibody 42 or GNP 49 to the circulating Aβ protein 52 in step 54, retrieval via catheter 14 to fractionation device 10 in step 56 and alternative magnetic separation method of the tagged antibody-protein complex from the CSF in a magnetic chamber or filter 16 in step 58. The cleansed CSF is returned to the subarachnoid space of the cranium or into the patient's abdomen through an output lumen of the catheter in step 60.

Alternatively, magnetic field effect fractionation of biological components from body fluids in general is a conventional method. For example, microfluidic devices are used to separate blood leukocytes by magnetic field effect fractionation of magnetically-labeled cells. Magnetic field effect fractionation has been used in stem cell sorting, immunoassays, bio-nanoparticles, biopolymers and proteomics. Two prior art examples of magnetic field effect fractionation of antibody-protein complexes using bacterial magnetic particles have been reported. Magnetic particles are chemically synthesized compounds of micrometer and nanometer sizes; however, the synthesis of these particles with uniform size and shape and good disparity in aqueous solutions remain challenging. On the other hand, magnetic bacteria consistently yield nano-sized magnetic particles which accounts for their use in some conventional methods.

In order to achieve clinical efficacy with an antibody in the treatment of Alzheimer's disease, Parkinson's disease or multiple sclerosis, an antibody must be able pass from the circulatory system into the brain. Gaining access to the brain; however, has proven challenging in most instances because the brain blood barrier (BBB) effectively blocks or limits such access. The evolutionary purpose of the blood brain barrier is to keep foreign substances from gaining access to the brain. In the absence of a blood brain barrier, bacteria could easily get into the brain and establish life-threatening brain infections. In addition, the blood brain barrier serves to facilitate and control the entry of certain substances critical to brain function. In essence, the blood brain barrier serves as a center for homeostasis for the brain. The MBP 10 can deliver an antibody into the brain and thereby achieve and maintain a therapeutically effective dose of the drug without the need for the antibody to ever cross the blood brain barrier. Moreover, the cerebral microdialysis embodiments outlined above present the first opportunity to remove an antibody-protein complex from the CSF without reliance on the Fc receptor-mediated clearance pathway.

Biofeedback Mechanism

Each of the embodiments of the MBP pumping system above may further optionally incorporate a biosensor, thereby providing a biofeedback mechanism to monitor levels of circulating Aβ protein in the patient's CSF. Criteria and guidelines were established in 2011 by the National Institute on Aging and the Alzheimer's Association, which identified two biomarker categories for Alzheimer's disease: (a) biomarkers showing the level of Aβ protein accumulation in the brain and (b) biomarkers showing that neurons in the brain are injured or degenerating. Sensors for such biomarkers could be developed as stand-alone companion devices or optionally incorporated into a MBP cerebral micro-dialysis device, employing a replaceable filter cartridge 38 functionalized with aptamer or antibody to detect such analyte proteins.

It can now be appreciated that the illustrated embodiments offer the following advantages:
a. Fully implantable device 10;
b. Three embodiments of usage: dialysis membrane or replaceable filter cartridge 16 impregnated with antibody 44, reversible electrostatic filter, or alternatively magnetic field effect fractionator of magnetically-tagged antibodies 48.

c. Option for metronomic delivery of the antibody to the brain, bypassing the blood brain barrier;
d. Routing of cleansed CSF to the cranium or the abdomen;
e. Minimal propensity for membrane or filter clogging;
f. Optional biofeedback mechanism of circulating disease protein levels; and
g. Construction using MRI compatible materials.

Cerebral microdialysis addresses the cause of the disease symptom leading to a decline in quality of life. Demonstrating a "cure" is thus not required as proof of clinical efficacy. Antibodies generally portray minimal risk of toxicity or adverse therapeutic effects because of their high degree of selectivity for the antigen relative to other endogenous molecules. Implantable device minimize risk of infection and offers higher quality of life options to the patient. The embodiments eliminate the need to achieve penetration of blood brain barrier by a therapeutic and are able to evaluate disease progression by measuring disease associated Aβ levels through biofeedback mechanism in addition to monitoring cognitive decline of the patient.

The technique of microdialysis enables sampling and collecting of small-molecular-weight substances from the interstitial space. It is a widely used method in neuroscience and is one of the few techniques available that permits quantification of neurotransmitters, peptides, and hormones. The application teaches a method and the underlying principles of the microdialysis process for estimating extracellular concentration from dialysis samples (i.e., relative recovery). The technique of microdialysis enables the monitoring of CSF accumulation of Aβ and other molecules 52 in interstitial tissue fluid. This method is widely used for sampling and quantifying neuropeptides in the brain and periphery. Depending on the availability of an appropriate analytical assay, virtually any soluble molecule in the interstitial space fluid can be measured by microdialysis. This unit describes the principles of conventional and quantitative microdialysis, as well as strategies for designing a dialysis experiment. Although the methods described are those used for monitoring CNS function, they can easily be adapted to other organ systems.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

TABLE 1

| Representative Alzheimer's disease Immunotherapy Programs | | | | | |
|---|---|---|---|---|---|
| Product Name | Company | Clinical Phase | Patient Population | Binding Domain | Therapeutic Target |
| Solanezumab | Eli Lilly | 3 | Prodromal and mild Alzheimer's disease | Aβ | Soluble Aβ |
| Gantenerumab | Roche | 2/3 | Prodromal and mild Alzheimer's disease | Combined Aβ N-terminal and mid domain, conformational | Aggregated Aβ |
| BAN2401 | Eisai/BioArctic Neuroscience/Eisai | 2b | MCI due to Alzheimer's disease or mild Alzheimer's disease | N-terminal, conformational | Soluble Aβ protofibrils |

TABLE 1-continued

Representative Alzheimer's disease Immunotherapy Programs

| Product Name | Company | Clinical Phase | Patient Population | Binding Domain | Therapeutic Target |
|---|---|---|---|---|---|
| Crenezumab | Genentech/Roche | 2 | Prodromal and mild/moderate Alzheimer's disease | Aβ | Soluble oligomeric/fibrillar Aβ and plaque |
| Bapineuzumab | Elan/Pfizer/Johnson & Johnson | Intravenous and subcutaneous programs terminated | Mild/moderate Alzheimer's disease | Aβ | Soluble and aggregated Aβ |
| (Aducanumab) BIIB037 | Biogen/Neuroimmune Therapeutics | 3 | MCI due to Alzheimer's disease or mild Alzheimer's disease | Conformational Aβ | Fibrillar Aβ |
| AAB003 | Elan/Pfizer/Janssen | 1 | Mild/moderate Alzheimer's disease | Aβ | Soluble and aggregated Aβ |
| SAR228810 | Sanofi | 1 | Mild/moderate Alzheimer's disease | Not published | Soluble oligomeric/protofibrillar Aβ |
| ABP102 | Abiogen Pharma | 1 | Alzheimer's disease | Catalytic antibody cleaving Aβ | Aggregated Aβ |
| Ponezumab | Pfizer | 1 | Mild/moderate Alzheimer's disease | Aβ | Soluble and aggregated Aβ |

We claim:

1. An apparatus for performing cerebral micro-dialysis to treat neurological disease of a patient's brain comprising:
   a catheter for implantation in or near the patient's brain;
   an implantable first pump communicated with the catheter configured to transport cerebrospinal fluid (CSF) from the patient, which CSF contains diseased cells or biomolecules associated with the neurological disease;
   an implantable separation device communicated with the first pump wherein the diseased cells or biomolecules are removed, where the separation apparatus includes a dialysis membrane impregnated with an antibody, a reversible electrostatic filter, and/or a magnetic field effect fractionation chamber wherein a magnetically-tagged antibody scavenges and aids in the removal of circulating diseased cells or biomolecules from the CSF; and
   an implantable second pump communicated with a drug reservoir and with the catheter configured to transport CSF and a medication to the patient.

2. The apparatus of claim 1 where the dialysis membrane impregnated with an antibody comprises a molecular recognition agent having high binding affinity and specificity for the diseased cells or biomolecules in the CSF.

3. The apparatus of claim 1 further comprising means for delivering a molecular recognition agent to a patient's biological fluid and removing a diseased associated antigen from the biological fluid by means of the formation of a molecular recognition agent-antigen complex.

4. The apparatus of claim 3 where the molecular recognition agent comprises an antibody, an aptamer or an oligomer.

5. The apparatus of claim 3 where the molecular recognition agent comprises a humanized monoclonal antibody having high specificity and selectivity for a disease-associated antigen.

6. The apparatus of claim 5 where the disease-associated antigen comprises a protein or cell associated with the neurological disease.

7. The apparatus of claim 6 where the disease-associated antigen comprises Aβ or tau protein.

8. The apparatus of claim 3 where the molecular recognition agent-antigen complex comprises an antibody-protein complex, an antibody-diseased cell complex, an aptamer-biomolecules complex, or an oligonucleotide-biomolecules complex.

9. The apparatus of claim 1 where the magnetically-tagged antibody of the magnetic field effect fractionation chamber comprises a magnetic particle attached to the antibody or attached through a monoclonal antibody linker.

10. The apparatus of claim 9 where the magnetic particle is an iron nanoparticle, composed of a non-toxic magnetic material, or a bacterial magnetic particle.

11. The apparatus of claim 1 where the magnetically-tagged antibody of the magnetic field effect fractionation chamber has a specificity and selectivity for a disease-associated antigen.

12. The apparatus of claim 1 further comprising an antibody storage reservoir for storing the magnetic particle-tagged antibody and a pump communicated with the antibody storage reservoir, which is communicated with the catheter for delivery of the magnetic particle-tagged antibody to the patient's CSF.

13. The apparatus of claim 12 where the antibody storage reservoir is disposed within the apparatus, or further comprises a cerebral shunt and is communicated with the cerebral shunt communicating with the catheter.

14. The apparatus of claim 1 further comprising an implantable magnetic capture reservoir and where the magnetic particle-tagged antibody-antigen complex is magnetic field effect fractionated within the magnetic capture reservoir.

15. The apparatus of claim 1 further comprising a T intersection disposed between the first pump and the second pump, where the first pump returns cleansed CSF to the T intersection and then to the patient to establish loop dialysis.

16. The apparatus of claim 15 where the cleansed CSF is returned from the magnetic capture reservoir via the catheter to a subarachnoid space of a patient's cranium or into a patient's abdomen.

17. The apparatus of claim 2 where the molecular recognition agent is impregnated on the membrane and comprises an antibody, an aptamer, an oligonucleotide, or a monoclonal antibody to Aβ or tau protein.

18. The apparatus of claim 17 further comprising a cartridge and where the impregnated membrane is included within the cartridge disposed within the apparatus, or further comprises a cerebral shunt and the cartridge is disposed within the cerebral shunt.

19. The apparatus of claim 18 where the cartridge includes multiple units of the impregnated membrane.

20. The apparatus of claim 1 where the reversible electrostatic filter captures circulating antigen from the CSF, where the circulating antigen is a protein having a positive charge, the reversible electrostatic filter has a negative charge for a predetermined time, and where the charge of the reversible electrostatic filter is reversed to a positive charge to release the protein from the reversible electrostatic filter.

21. The apparatus of claim 1 further comprising a biosensor to detect and to generate a biofeedback regarding disease progression and regression by monitoring levels of a disease-associated antigen present in the patient's CSF.

22. The apparatus of claim 21 where the biosensor is separated and operates independently from other elements of the apparatus.

23. The apparatus of claim 21 where the biosensor is included within the apparatus.

24. The apparatus of claim 21 where biosensor to detect and to generate a biofeedback regarding Aβ or tau protein.

25. The apparatus of claim 1 where the catheter, pump and separation device are composed of MRI compatible material.

26. A method comprising:
cranially implanting a microdialysis device in a patient, where the microdialysis device includes: a ventricular catheter; pump tubing; a first pump which further includes a separation device; and a second pump communicated with a drug reservoir;
inserting the ventricular catheter into a right frontal horn of a lateral ventricle of the patient;
anchoring the ventricular catheter to a cranial periosteum of the patient, the ventricular catheter having a port for CSF sampling;
pumping CSF to the dialysis membrane from the ventricular catheter through the pump tubing;
cleansing the CSF with the separation device;
mixing the cleansed CSF with a medication from the drug reservoir within the pump tubing; and
returning the mixed cleansed CSF and medication via the pump tubing back into the ventricle.

27. The method of claim 26 where cleansing the CSF with the separation device comprises cleansing the CSF using a dialysis member containing impregnated antibodies, using a reversible electrostatic filter, and/or a separation chamber wherein a magnetically-charged antibody is removed from the CSF via magnetic field effect fractionation.

28. The method of claim 27 where cleansing the CSF using a dialysis member containing impregnated antibodies comprises cleansing the CSF using antibodies for conjugating Amyloid-Beta or Tau protein.

29. The method of claim 28 where cleansing the CSF using antibodies for conjugating Amyloid-Beta or Tau protein comprises using a dialysis member functionalized with capture probes linked to gold nanoparticles via linker molecules to form a complex probe with affinity for recovery of Amyloid-Beta or Tau protein.

30. The method of claim 27 where cleansing the CSF using a dialysis member containing impregnated antibodies comprises cleansing the CSF using antibodies for conjugating a predetermined analyte.

31. The method of claim 30 where cleansing the CSF using antibodies for conjugating the predetermined analyte comprises using a dialysis member functionalized with capture probes linked to gold nanoparticles via linker molecules to form a complex probe with affinity for recovery of the predetermined analyte.

* * * * *